United States Patent
Yamamoto et al.

(10) Patent No.: US 7,273,697 B2
(45) Date of Patent: Sep. 25, 2007

(54) METHOD FOR ANALYZING BASE SEQUENCE OF NUCLEIC ACID

(75) Inventors: Nobuko Yamamoto, Kanagawa (JP); Tadashi Okamoto, Kanagawa (JP); Tomohiro Suzuki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/942,596

(22) Filed: Aug. 31, 2001

(65) Prior Publication Data

US 2002/0168648 A1     Nov. 14, 2002

(30) Foreign Application Priority Data

Aug. 31, 2000    (JP)    ............... 2000-263506

(51) Int. Cl.
*C12Q 1/68* (2006.01)
*C12P 19/34* (2006.01)

(52) U.S. Cl. .......................... 435/6; 435/91.2
(58) Field of Classification Search ............ 435/6, 435/91.2; 536/22.1, 23.1; 702/19, 20
See application file for complete search history.

(56) References Cited

U.S. PATENT DOCUMENTS

| | | | |
|---|---|---|---|
| 5,202,231 A | 4/1993 | Drmanac et al. ............ | 435/6 |
| 5,445,934 A | 8/1995 | Fodor et al. ............ | 435/6 |
| 5,733,729 A | 3/1998 | Lipshutz ............ | 435/6 |
| 6,027,880 A | 2/2000 | Cronin et al. ............ | 435/6 |
| 6,228,575 B1 * | 5/2001 | Gingeras et al. ............ | 435/5 |

FOREIGN PATENT DOCUMENTS

| | | |
|---|---|---|
| EP | 0 717 113 A2 | 6/1996 |
| EP | 0 995 804 A2 | 4/2000 |
| WO | WO95/11995 | 5/1995 |

OTHER PUBLICATIONS

Gennady Yershov et al., "DNA Analysis and Diagnostics on Oligonucleotide Microchips," 93 *Proc. Natl. Acad Sci.* 4913-4918 (1996).
David G. Wang et al., "Large-Scale Identification, Mapping and Genotyping of Single-Nucleotide Polymorphisms in the Human Genome," 280 *Science* 1077-1082 (1998).
Mark Chee et al., "Accessing Generic Information with High-Density DNA Arrays," 274 *Science* 610-614 (1996).
William I. Wood et al., "Base Composition-Independent Hybridization in Tetramethylamonium Chloride: A Method for Oligonucleotide Screening of Highly Complex Gene Libraries," 82 *Proc. Natl. Acad. Sci USA* 1585-1588 (1985).

* cited by examiner

*Primary Examiner*—Jeffrey Fredman
(74) *Attorney, Agent, or Firm*—Fitzpatrick, Cella, Harper & Scinto

(57) ABSTRACT

A method for identifying an unknown base sequence present in a target single-stranded nucleic acid utilizing a probe array in which single-stranded nucleic acid probes are arranged as isolated spots on a substrate, where each probe has a base sequence complementary to one of the plural base sequences expected to be the unknown base sequence, and a fluorescence pattern of a sample on the probe array is compared with template patterns to identify the base sequence of the sample.

6 Claims, 7 Drawing Sheets

FIG. 1

Top sequences (left to right):
GATGGGCCTCAANGTTCAT
GATGGGCCTCGCNGTTCAT
GATGGGCCTCCCNGTTCAT
GATGGGCCTCTONGTTCAT
GATGGGTCTCAANGTTCAT
GATGGGTCTCGGNGTTCAT
GATGGGTCTCCCNGTTCAT
GATGGGTCTCTTNGTTCAT Bottom sequences (left to right):
GATGGGACTCAANGTTCAT
GATGGGACTCGCNGTTCAT
GATGGGACTCCCNGTTCAT
GATGGGACTCTTNGTTCAT
GATGGGGCTCAANGTTCAT
GATGGGGCTCGGNGTTCAT
GATGGGGCTCCCNGTTCAT
GATGGGGCTCTTNGTTCAT Grid (left labels A G C T / A G C T; top labels A G C T / A G C T):

| | A | G | C | T | A | G | C | T |
|---|---|---|---|---|---|---|---|---|
| A | 1 | 5 | 9 | 13 | 17 | 21 | 25 | 29 |
| G | 2 | 6 | 10 | 14 | 18 | 22 | 26 | 30 |
| C | 3 | 7 | 10 | 15 | 19 | 23 | 27 | 31 |
| T | 4 | 8 | 12 | 16 | 20 | 24 | 28 | 32 |
| A | 33 | 37 | 41 | 45 | 49 | 53 | 57 | 61 |
| G | 34 | 38 | 42 | 46 | 50 | 54 | 58 | 62 |
| C | 35 | 39 | 43 | 47 | 51 | 55 | 59 | 63 |
| T | 36 | 40 | 44 | 48 | 52 | 56 | 60 | 64 |

METHOD FOR ANALYZING BASE SEQUENCE OF NUCLEIC ACID

BACKGROUND OF THE INVENTION

1. Field of the Invention

The present invention relates to a method of identifying the base sequence of a nucleic acid by using a DNA chip for DNA diagnosis and medical treatment.

2. Related Background Art

One of the techniques for sequencing a nucleic acid, etc. or for detecting the sequence is to utilize a DNA array. U.S. Pat. No. 5,445,934 discloses a DNA array where 100,000 or more oligonucleotide probes are bonded in 1 inch square. Such a DNA array has an advantage in that many characteristics can be examined at the same time with a very small sample amount. When a fluorescence-labeled sample is poured onto such a DNA chip, DNA fragments in the sample bind to probes having a complementary sequence fixed on the DNA chip, and only that part can be discriminated by fluorescence to elucidate the sequence of the DNA fragment in the DNA sample.

Sequencing By Hybridization (SBH) is a method for examining the base sequence utilizing such a DNA array and the details are described in U.S. Pat. No. 5,202,231. In the SBH method, all possible sequences of an oligonucleotide of a certain length are arranged on the substrate, then fully matched hybrids formed by a hybridization reaction between probes and the sample DNA are detected. If a set of fully matched hybrids is obtained, the set will give an assembly of overlapping sequences with one base shift being a part of one certain sequence, of which analysis will elucidate that sequence.

In principle, in order to examine whether or not a certain sequence is present in a DNA specimen, a hybridization reaction is carried out with a prove having a complementary sequence, and the presence or absence of hybridization is detected. In practice, however, it is very difficult to judge the presence or absence of one sequence by using one complementary probe and hybridization, because even when fully matched hybrids are compared, the fluorescence intensities of the hybrids differ from each other according to their sequence. In particular, GC content in the sequence greatly affects the stability of the hybrid. Further, sequences not exactly complementary but containing one base mismatch also form a hybrid to emit fluorescence. Such a hybrid has lower stability and weaker fluorescence compared with a fully matched hybrid of the same sequence, but it is often observed that such a mismatch hybrid has a stronger fluorescence than a full-matched hybrid of a different sequence. In addition, the stability of one mismatch hybrid greatly varies according to the location of the mismatch in the hybrid. When the mismatch is located at the terminus, a relatively stable hybrid is obtained. When the mismatch is located at the center of the hybrid, the hybrid becomes unstable because the consecutiveness of the complementary strand is broken. Thus, at present, various factors are participating in the hybrid stability, and the absolute value (standard value) for the fluorescence intensity, to judge whether or not the hybrid is full matched, is not obtained. Also, conditions for detecting the fluorescence solely from the full matched hybrid, eliminating fluorescence from one-base mismatched hybrids, have not been determined.

In order to eliminate the difference of the hybrid stability due to the sequence, a method using tetramethylammonium chloride is described in Proc. Natl. Acad. Sci. USA Vol. 82, pp. 1585-1588 (1985). However, the above-described problems have not been solved perfectly.

A method for judging whether a hybrid is a perfect match is described in Science vol. 274 p. 610-614, 1996, in which a 15-mer oligonucleotide probe and 15-mer oligonucleotides having the same sequence except for one mismatching base at the center of the sequence are prepared. The fluorescence intensity of the hybrid with the probe (perfect match) is compared with those of hybrids with other one-base mismatching oligonucleotides. Only when the intensity of the perfect match is stronger, it is judged positive.

Based on the method above, U.S. Pat. No. 5,733,729 discloses a method using a computer for a more accurate calling, where the fluorescence intensities of the hybrids are compared by using a computer to know the base sequence of a sample.

In these methods, it is necessary to locate the subject nucleotide to be examined in the center of a probe and to prepare a set of four probes each having one of four bases at the position. It is also necessary to prepare such a probe set for each of the overlapping sequences with one base shift. As described above, they use 15-mer oligonucleotides and determine the perfect match by comparing with other three types of probes having one-base mismatch at the center. It is said that more accuracy can be obtained by evaluating the stability of the hybrids theoretically or empirically. In addition, if the base length of the region to be examined is L, the number of probes will be 4×L (e.g., 20 probes for 5 bases).

Although the above-described methods using mismatches are excellent in that the call is relatively easy by comparing with one-base mismatches at the same position of the same sequence and that the number of probes may be small (in SBH, 1024 types of probes are required for the similar analyses), they have significant defects in that accurate information cannot be obtained when there are two base mismatches in the same region or when there is a base deletion or insertion.

On the other hand, the SBH method may solve the above-described problems and in principle, it may cope with any variation. A call, however, is rather difficult, because the intensity of a one-base mismatch in one sequence is stronger than that of a full match in another sequence and because stability of the hybrid differs considerably according to the position of the mismatch in the sequence even if it is an one-base mismatch. As a result, a full match, one-base and two-base mismatches (continuous or discontinuous) cannot be simply called from the fluorescence intensities. Accordingly, complex analyses, including theoretical predictions, comparison between individual sequences and accumulation of empirical parameters, are required.

Furthermore, in order to determine the sequence of a gene by reading fluorescence intensities of hybrids for each probe followed by data analysis, a large-scale computer system as well as a detector for reading arrays are required. This is a big obstacle in the way of simple gene diagnosis using the DNA array.

SUMMARY OF THE INVENTION

In view of such problems, the present invention provides a method of accurate gene sequencing not requiring complex analyses.

As described above, the fluorescence intensity of a hybrid is controlled by various factors. Thus, when a probe having about 12 mer to 25 mer in length is used, it is hard to exclude the fluorescence due to hybrids having a one-base mismatch.

On the other hand, it is relatively easy to obtain the conditions for inhibiting formation of two-base mismatch hybrids regardless of position, continuity or discontinuity of the two-base mismatch, when a probe of 12 mer to 25 mer in length is used.

The present invention has been achieved based on such a finding characterized in that spots of mismatch hybrids containing a predetermined number of mismatches are taken into account as well as a spot of a perfect match hybrid.

According to one embodiment of the present invention, there is provided a method for identifying an unknown base sequence present in a target single-stranded nucleic acid comprising the steps of:

(a) preparing a probe array in which single-stranded nucleic acid probes of No. 1 to No. n (n≧2) are arranged as isolated spots on a substrate, the probes each having a base sequence complementary to one of the plural base sequences expected to be the unknown base sequence;

(b) reacting a single-stranded nucleic acid, which has a base sequence fully complementary to a base sequence of one of the single-stranded nucleic acid probes and is fluorescence-labeled, with the probe array under such conditions that single-stranded nucleic acids complementary to each other form a double-stranded nucleic acid;

removing the unreacted labeled single-stranded nucleic acid, and measuring fluorescence intensity of each spot of the probe array to obtain a first template pattern showing a relationship between location of the probes and fluorescent characteristics;

(c) performing the same operation as in step (b) for each of the remaining single-stranded nucleic acid probes using a second to a nth single-stranded nucleic acid, and obtaining template patterns of No. 2 to No. n showing a relationship between location and fluorescent characteristics of the probes;

(d) performing the same operation as in step (b) using a sample containing the target single-stranded nucleic acid of an unknown base sequence to obtain a sample pattern showing a relationship between a position and fluorescent characteristics; and (e) comparing the sample pattern obtained in step (d) with n pieces of template patterns obtained in steps (b) and (c) to identify a template pattern showing substantially the same pattern as the sample pattern and identifying the base sequence of the single-stranded nucleic acid used for the preparation of the identified template pattern as the unknown base sequence of the target single-stranded nucleic acid.

According to another embodiment of the present invention, there is provided a method for identifying an unknown base sequence present in a target single-stranded nucleic acid comprising the steps of:

(a) preparing a probe array in which single-stranded nucleic acid probes of No. 1 to No. n (n≧2) are arranged as isolated spots on a substrate, the probes each having a base sequence complementary to one of the plural base sequences expected to be the unknown base sequence;

(b) reacting a single-stranded nucleic acid, which has a base sequence fully complementary to a base sequence of one of the single-stranded nucleic acid probes and is fluorescence-labeled, with the probe array under such conditions that single-stranded nucleic acids complementary to each other form a double-stranded nucleic acid;

removing the unreacted labeled single-stranded nucleic acid, and measuring fluorescence intensity of each spot of the probe array to obtain a first template pattern showing a relationship between the location of the probes and fluorescent characteristics;

(c) analyzing the first template pattern to locate probes and to calculate a mean value of fluorescence intensities (Fi) of the double-stranded nucleic acids having i of mismatched base pairs, where i is an integer not less than 1;

(d) calculating a difference (F1, 0) between the fluorescence intensity of the fully complementary double-stranded nucleic acid without mismatch (F0) and the mean value of the fluorescence intensities of the double-stranded nucleic acids having a one-base mismatch (F1), further calculating a difference (Fi+1, i) between a fluorescence intensity of a double-stranded nucleic acid having (i+1) base mismatches (Fi+1) and a fluorescence intensity of a double-stranded nucleic acid having i-base mismatches (Fi), and identifying i being Fi+1, i<<Fi, i−1;

(e) assuming a target DNA, which base sequence is complementary to the second probe sequence, then obtaining the second template pattern formed by the probe position where the number of mismatched base pairs to the target having the complementary sequence to the second probe sequence is not more than i;

(f) performing the same operation as in step (e) for each of the remaining single-stranded nucleic acid probes using a third to a nth single-stranded nucleic acid, and obtaining template patterns of No. 3 to No. n showing a relationship between the location and fluorescent characteristics of the probes, wherein the template patterns are formed from the positions of the probes having a base sequence that forms mismatched base pairs in a number not more than i;

(g) performing the same operation as in step (b) using a sample containing the target single-stranded nucleic acid of an unknown base sequence to obtain a sample pattern showing a relationship between a position and fluorescent characteristics; and (h) comparing the sample pattern obtained in step (g) with n pieces of template patterns obtained in steps (b), (c) and (e) to identify a template pattern showing essentially the same pattern as the sample pattern and identifying the base sequence of the single-stranded nucleic acid used for the preparation of the identified template pattern as the unknown base sequence of the target single-stranded nucleic acid.

According to the present invention, patterns of positive spots on the substrate are taken as images, and, the unknown sequence can be analyzed by comparing the images with the predicted pattern to identify the unknown genetic sequence easily.

Hybridization conditions, which allow complete discrimination between one-base mismatch and two-base mismatch are also disclosed.

BRIEF DESCRIPTION OF THE DRAWINGS

FIG. 1 shows a pattern of an arrangement when 64 types of probes are used;

DETAILED DESCRIPTION OF THE INVENTION

The present invention is explained in detail.

Call Using Fluorescence Image

One embodiment of the present invention particularly effective when bases which may cause mismatching exist close to each other. Herein, this will be explained using 5'GATGGGNCTCNNGTTCAT3' as an example, this sequence includes a base sequence corresponding to the 248th and 249th amino acids (hereinafter AA248 and AA249) of tumor suppressor gene p53. This example is only to explain this invention roughly, not to limit the present invention to a specific array form or probe arrangement. The concept of the present invention that the result is treated as an image is applicable to any form of arrays. The SBH method is naturally subjected to the analysis of the present invention.

In the above example, when a full set of probes is prepared by replacing the base represented by N with any of four bases (A, G, C, T), that is, when three bases (no need for continuity) are examined, $4^3=64$ probes are arranged on the substrate. $4^5=1024$ probes are required to examine five bases.

An example of the arrangement when 64 types of probes are used is shown in FIG. 1.

In this example, in the upper left quarter of the array of 64 probes, are arranged the probes of which the first N is A (probe number: 1-16), while in the lower left quarter, the probes of which the first N is G (probe number: 17-32). Similarly, in the upper right quarter, probes of which the first N is C (probe number: 33-48) are arranged and in the lower right, those having the first N of T (probe number: 49-64). In each region, the probes having the second N of A are positioned in the first column from the left, G, C and T for the second, third and fourth columns, respectively. Also, probes having the third N of A are positioned in the first row from the top in each region, G, C and T in the second, third and fourth rows, respectively. As a result, for example, the sequence of 5'GATGGGACTCAAGTTCAT3' corresponds to the upper left corner spot. A target nucleic acid being 5'ATGAACCGGAGGCCCATC3', which corresponds to the normal gene, is expected to form a hybrid with a probe DNA 5'GATGGGCCTCCGGTTCAT3', which is positioned at the cross-point of the third column from the right and the third row from the top.

Figure 2:
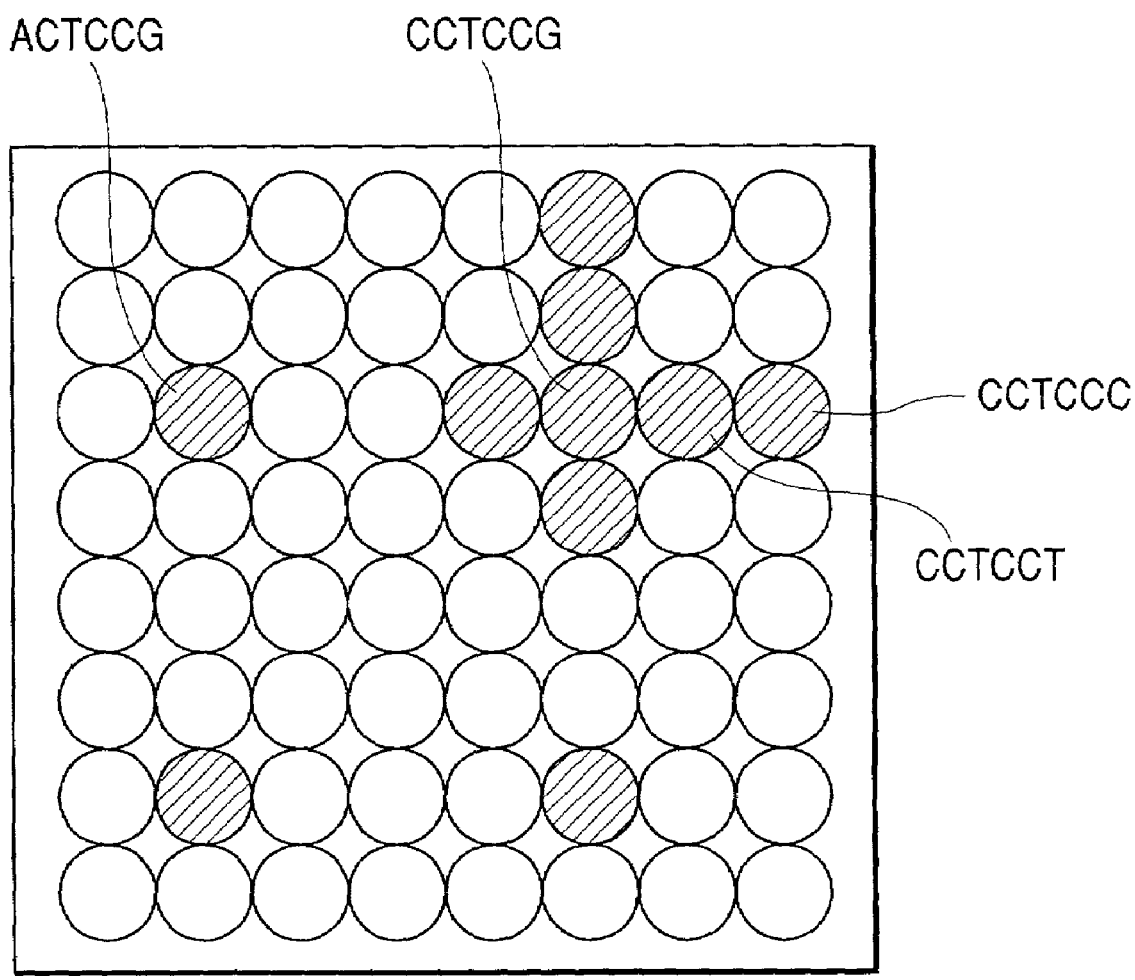
FIG. 2 shows a pattern of the arrangement showing positive spots formed with a target nucleic acid.

Now the case where one-base mismatches are included in a template pattern for determining the sequence of the gene will be explained. In this case, if the fully matching sequence is the probe 42 (normal), one-base mismatching sequences to be called positive correspond to 9 points (shadowed circles), forming a pattern together with the perfect match point as shown in FIG. 2.

Figure 3:
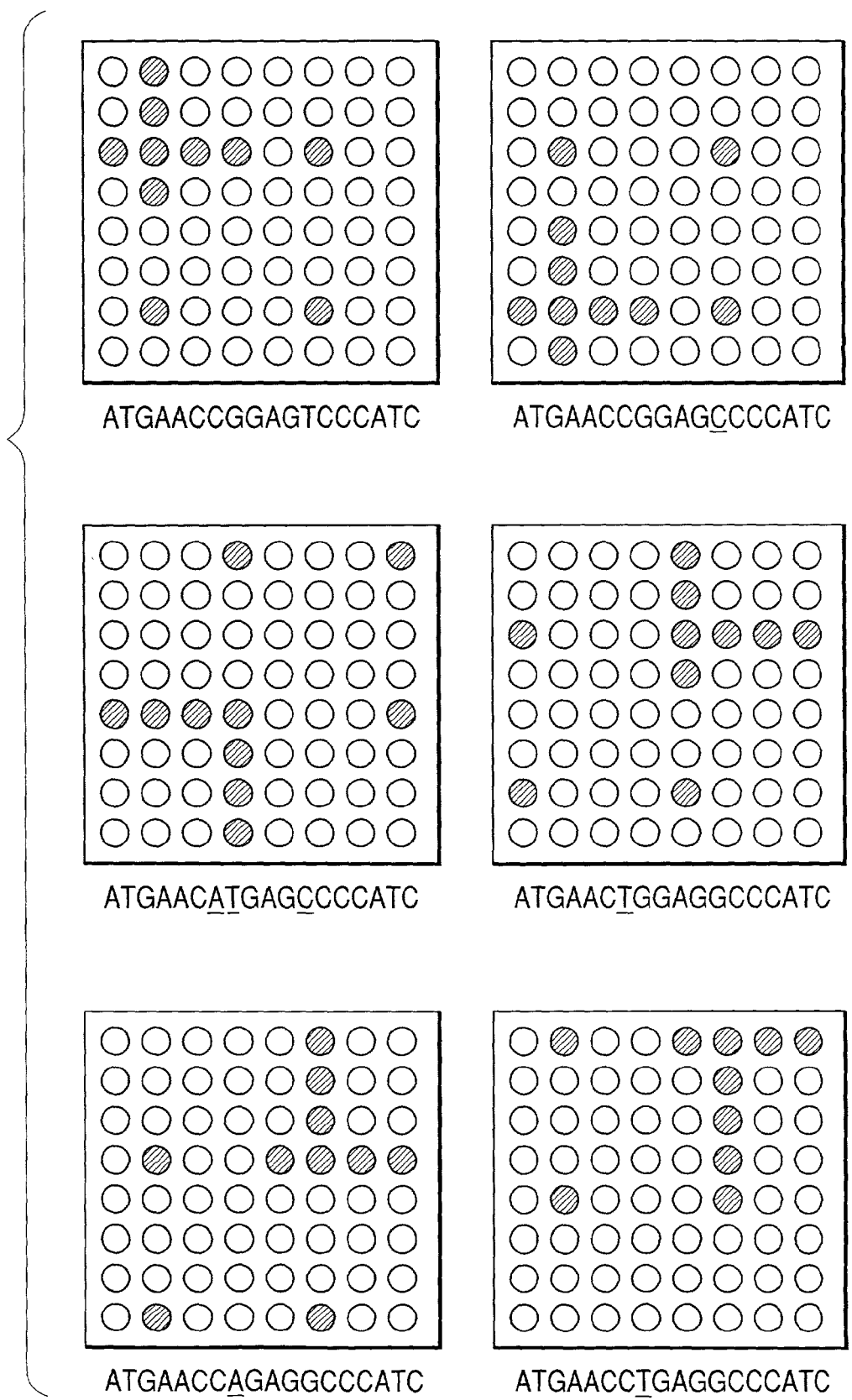
FIG. 3 shows patterns of the arrangement showing positive spots formed with variant sequences of the target nucleic acid.

On the other hand, the pattern change is observed with a target nucleic acid having a variant sequence to be identified, as shown in FIG. 3.

In the present invention, images of the expected fluorescent patterns composed of such full match and one-base mismatch hybrids are input into a computer memory device or the like beforehand, and the call is performed by comparing the fluorescent image obtained by a predetermined method with the memory. Herein, detailed quantitative data of the fluorescence intensity of positive spots is not required. Simple judgement on whether the fluorescence is stronger than the threshold value that has been determined experimentally enables simple and automatic calling using a computer, etc.

Setting of Threshold

When a probe of about 18 mer is used, the threshold is preferably set between the fluorescence intensity of the one-base mismatch and that of the two-base mismatch. Although the fluorescence intensity depends on the sequence or the reaction conditions, 50% to 25%, more preferably 30% to 20%, of the highest fluorescent intensity (normally of the full match hybrid) may be used as the threshold. When the length of the probe is shorter, the threshold will be lower.

Fluorescence of those having three-base mismatch will be below 10% of the maximum fluorescence, allowing complete discrimination.

Figure 4:
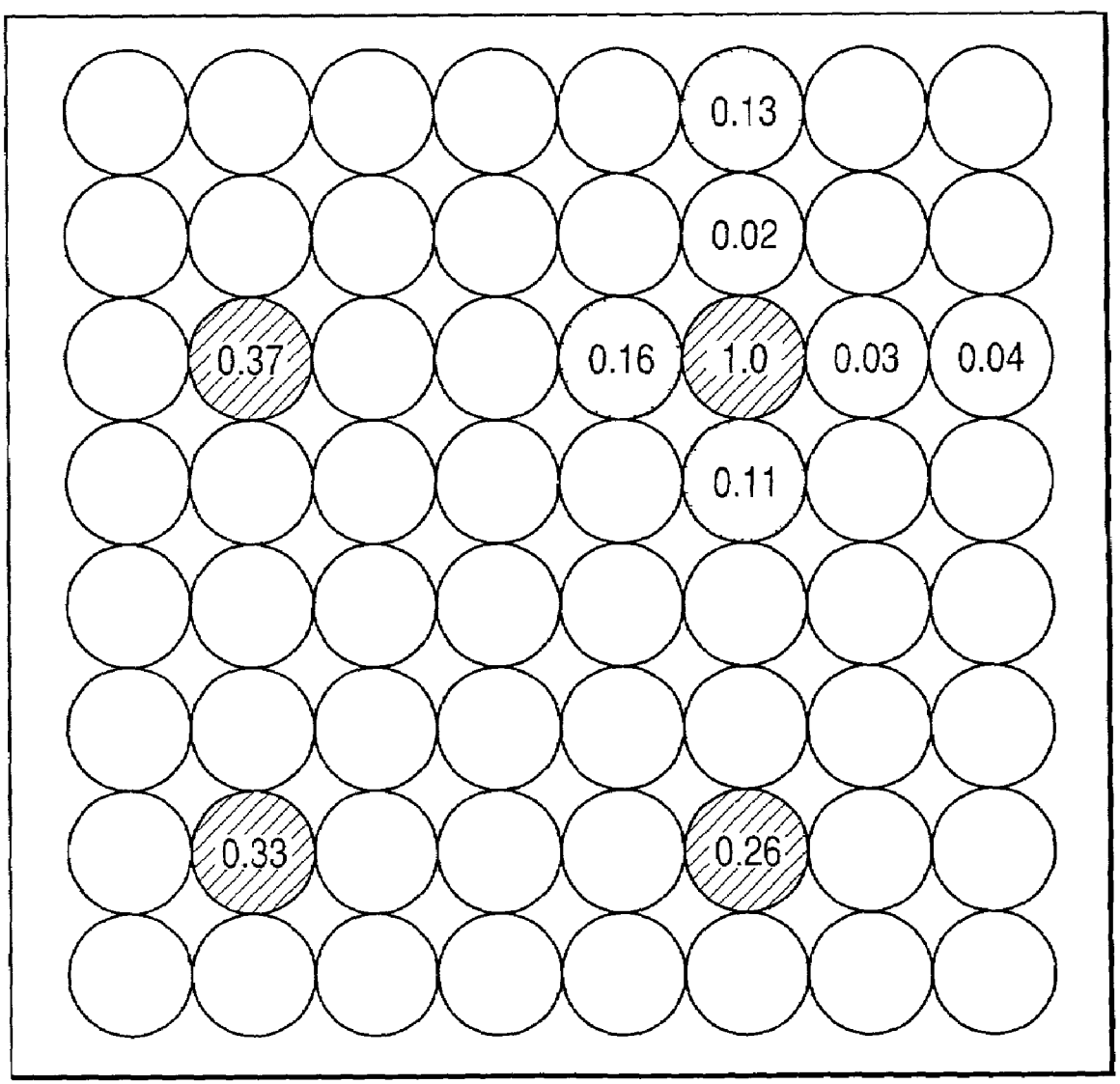
FIG. 4 shows is a pattern obtained in Example 1 with fluorescence intensities.

FIG. 4 shows the spots that fluoresce at an intensity higher than 10% of the maximum fluorescence corresponding to the full match and one-base mismatch hybrids.

A more specific calling method will be described with the above example.

When the hybridization reaction is carried out very selectively, strong fluorescence appears only at one point (the full match). When the sensitivity is increased gradually or the stringency in reaction conditions is reduced, as expected from FIG. 3 in the above-arranged example, the one-base mismatch points will appear in a row and a column crossing at the full match point. However, the actual fluorescent image is not always such that three spots each align in a row and column around a strong fluorescent point. Since six points not always have a similar fluorescence intensity due to the hybrid stability difference, not all of the spots can be detected. However, at least some spots would be seen on those lines. At the same time, the remaining one-base mismatches may fluoresce at the expected positions, although the intensity might be weaker than other spots.

Sometimes, the full match hybrid and one-base mismatch hybrids may have a similar fluorescence intensity to give a pattern consisting of the expected 10 spots of the full match and one-base mismatches.

Although the fluorescence intensity of two-base mismatch hybrids sometimes exceeds the threshold, they can be distinguished easily because of the divergence from the expected pattern.

Thus, the method of the present invention where calling is performed by comparing the expected pattern with the actually obtained fluorescent image has a feature that the presence or absence of a variation in the test gene can be easily determined and, at the same time, the nature of the variation (which base(s) is changed to what base(s)) can be determined.

Further, when the result of hybridization using 64 probes is assessed, the idea of pattern assessment has an advantage in that calling is more reliable than with only one spot. Since the hybrids with 64 DNA probes differ in heat stability between individual sequences, it is not guaranteed that the full match hybrid is always far more stable and radiates a stronger fluorescence. In addition, it is often impossible to determine the strongest and full match spot due to the foreign matter on the substrate or the artifacts during the hybridization reaction. At this point, calling by a pattern can compensate for a certain variation of fluorescence intensity, if any.

Probe length

The probe length used for the present invention is approximately 8 mer to 30 mer, more preferably 12 mer to 25 mer. When it is shorter than 8 mer, stability of the hybrids having a one-base mismatch is low and the fluorescence from the full match is superior, while when it is longer than 30 mer, the fluorescence of two-base mismatches sometimes is (for example, when mismatches locate at the both ends) stronger than that of one-base mismatches.

Conditions of Hybridization Reaction

Preferable hybridization conditions are as follows: A substrate is soaked completely in a sample solution and heated for heat-denaturing both the DNA probes on the substrate and the sample DNA. Then, the substrate and the solution are cooled slowly to perform the hybridization reaction. The salt concentration of the reaction mixture without formamide is desirably below 100 mM.

An appropriate temperature for heat denaturation is 60° C. or higher, preferably 80° C. or higher. The temperature for heat denaturation is determined depending on the stability of the substrate itself, length and concentration of the test DNA, and type of the labeling compound. For example, with such a substrate prepared by binding DNA to a resin layer formed on the surface of the substrate, sometimes the resin layer is destroyed by heating at a high temperature. On the other hand, substrates prepared using a silane coupling agent are rather heat-stable and can be heated to a higher temperature. When the test DNA is a single-stranded DNA, the intramolecular double-stranded structure melts at 70° C. or more, while when the sample is a double-stranded DNA or long single-stranded DNA, it is necessary to melt the double-stranded structure by heating at a higher temperature or by adding a denaturing agent such as formamide. Time required for heat denaturation is 10 min or more, depending on the microassay size and the volume of the sample solution.

The hybridization conditions are determined according to the conventional method where temperature and salt concentration are changed considering the length and sequence of the probes, and the type of the test sample. The suitable conditions for discriminating extremely similar sequences as in the present invention are 45° C. for over 3 hours in a solution containing 100 mM of sodium chloride. However, as the reaction time is greatly affected by the sample concentration, it is not limited to the above reaction conditions. With a sample of a high concentration, calling within 3 hours is possible, while with a dilute sample, 10 hours or more of the reaction time are required. When formamide is added, the concentration of sodium chloride should be increased.

Preparation of DNA Array

How to prepare the DNA array suitable for the hybridization reaction of the present invention is exemplified below. However, since the purpose of the present invention is to provide a simple method for evaluating the hybridization pattern on the substrate to determine the base sequence of a sample, the substrate preparation method is not specifically limited.

DNA probes may be covalently bonded to the substrate by reacting the probes with functional groups on the substrate. The following is a method of a coupling reaction between a maleimide group on the glass surface with an SH group at the end of DNA.

Maleimide groups can be incorporated onto the surface of a substrate, first, by introducing amino groups with an amino silane coupler onto the substrate, and then reacting the amino groups with a reagent containing N-(6-maleimidocaproyloxy)succinimide (EMCS reagent: Dojin Co., Ltd.). Introduction of an SH group to the DNA can be performed by using a 5'-Thiol-Modifier C6 (Glen Research Company) on a DNA-automatic synthesizer.

Spots of the DNA probes are formed on the substrate by the ink jet method. Then, the probe DNA is fixed by the reaction between the maleimide groups on the substrate and the SH groups at the end of the DNA.

A DNA solution suitable for ink jet ejection to the maleimide-substrate is one containing glycerin, urea, thiodiglycol or ethylene glycol, acetylenol EH (Kawaken Fine Chemical Company-made) and isopropyl alcohol. Particularly, a solution containing 7.5% of glycerin, 7.5% of urea, 7.5% of thiodiglycol and 1% of acetylenol EH is preferable.

The array substrate to which DNA has been bonded is then soaked in an aqueous solution of 2% bovine serum albumin for 2 hours for blocking. Then, it is ready for a hybridization reaction.

EXAMPLES

The invention will be described in the following Examples in more detail.

Example 1

Pattern Recognition I

1. Probe Design

It is well known that in the base sequence CGGAGG corresponding to the AA248 and AA249 of the tumor suppressor gene p53, frequently observed variations are the first C to T, the second A to G for AA248, and the third G to T for AA249. Accordingly, aiming at these three positions, 64 types of probes were designed.

That is, the designed nucleic acid are 18-mer nucleic acids harboring variegated above-mentioned six bases sandwiched between the common sequences, to be represented by 5'ATGAACNNGAGNCCCATC3' where N corresponds to any of 4 bases, A, G, C and T. Actual probes to detect the above sequence should have a complementary sequence of 5'GATGGGNCTCNNGTTCAT3'.

FIG. 1 shows an arrangement of 64 types of DNA probes on a substrate. Each sequence (SEQ ID NOs: 1 to 64) is specifically shown in Table 1.

TABLE 1

| Sequence Number (SEQ ID NO:) | Sequence |
| --- | --- |
| 1 | GATGGGACTCAAGTTCAT |
| 2 | GATGGGACTCAGGTTCAT |
| 3 | GATGGGACTCACGTTCAT |
| 4 | GATGGGACTCATGTTCAT |
| 5 | GATGGGACTCGAGTTCAT |
| 6 | GATGGGACTCGGGTTCAT |
| 7 | GATGGGACTCGCGTTCAT |
| 8 | GATGGGACTCGTGTTCAT |
| 9 | GATGGGACTCCAGTTCAT |
| 10 | GATGGGACTCCGGTTCAT |
| 11 | GATGGGACTCCCGTTCAT |
| 12 | GATGGGACTCCTGTTCAT |
| 13 | GATGGGACTCTAGTTCAT |
| 14 | GATGGGACTCTGGTTCAT |
| 15 | GATGGGACTCTGGTTCAT |
| 16 | GATGGGACTCTTGTTCAT |
| 17 | GATGGGGCTCAAGTTCAT |
| 18 | GATGGGGCTCAGGTTCAT |
| 19 | GATGGGGCTCACGTTCAT |
| 20 | GATGGGGCTCATGTTCAT |
| 21 | GATGGGGCTCGAGTTCAT |

TABLE 1-continued

| Sequence Number (SEQ ID NO:) | Sequence |
|---|---|
| 22 | GATGGGGCTCGGGTTCAT |
| 23 | GATGGGGCTCGCGTTCAT |
| 24 | GATGGGGCTCGTGTTCAT |
| 25 | GATGGGGCTGCAGTTCAT |
| 26 | GATGGGGCTCCGGTTCAT |
| 27 | GATGGGGCTCCCGTTCAT |
| 28 | GATGGGGCTCCTGTTCAT |
| 29 | GATGGGGCTCTAGTTCAT |
| 30 | GATGGGGCTCTGGTTCAT |
| 31 | GATGGGGCTCTCGTTCAT |
| 32 | GATGGGGCTCTTGTTCAT |
| 33 | GATGGGCCTCAAGTTCAT |
| 34 | GATGGGCCTCAGGTTCAT |
| 35 | GATGGGCCTCACGTTCAT |
| 36 | GATGGGCCTCATGTTCAT |
| 37 | GATGGGCCTCGAGTTCAT |
| 38 | GATGGGCCTCGGGTTCAT |
| 39 | GATGGGCCTCGCGTTCAT |
| 40 | GATGGGCCTCGTGTTCAT |
| 41 | GATGGGCCTCCAGTTCAT |
| 42 | GATGGGCCTCCGGTTCAT |
| 43 | GATGGGCCTCCCGTTCAT |
| 44 | GATGGGCCTCCTGTTCAT |
| 45 | GATGGGCCTCTAGTTCAT |
| 46 | GATGGGCCTCTGGTTCAT |
| 47 | GATGGGCCTGTCGTTCAT |
| 48 | GATGGGCCTCTTGTTCAT |
| 49 | GATGGGTCTCAAGTTGAT |
| 50 | GATGGGTTCTAGGTTCAT |
| 51 | GATGGGTCTCACGTTCAT |
| 52 | GATGGGTCTCATGTTCAT |
| 53 | GATGGGTCTCGAGTTCAT |
| 54 | GATGGGTCTCGGGTTCAT |
| 55 | GATGGGTCTCGCGTTCAT |
| 56 | GATGGGTCTCGTGTTCAT |
| 57 | GATGGGTCTCCAGTTCAT |
| 58 | GATGGGTCTCCGGTTCAT |
| 59 | GATGGGTCTCCCGTTCAT |
| 60 | GATGGGTCTCCTGTTCAT |
| 61 | GATGGGTCTCTAGTTCAT |
| 62 | GATGGGTCTCTGGTTCAT |
| 63 | GATGGGTCTCTCGTTCAT |
| 64 | GATGGGTCTCTTGTTCAT |

5' ATGAACCGGAGGCCCATC3', which is the sequence corresponding to the normal gene, is expected to form a hybrid with the DNA probe 42 of 5'GATGGGCCTCCGGT-TCAT3' located at the third point from the right and from the top.

In an experiment of 64 hybrid formation, fluorescence from the one-base mismatch hybrids is also expected in addition to that from the full match hybrid. An expected pattern of the fluorescence from the full match hybrid and one-base mismatch hybrids is shown in FIG. 2.

2. Preparation of Substrate Introduced with Maleimide Group

Substrate Cleaning

A 1 inch square glass plate was placed in a rack and soaked in an ultrasonic cleaning detergent overnight. Then, after 20 min of ultrasonic cleaning, the detergent was removed by washing with water. After rinsing the plate with distilled water, ultrasonic treatment was repeated in a container filled with distilled water, for additional 20 min. Then, the plate was soaked in a prewarmed 1N sodium hydroxide solution for 10 min, washed with water and then distilled water.

Surface treatment

The plate was soaked in an aqueous solution of a 1% silane coupling agent (product of Shin-Etsu Chemical Industry: Trade name KBM 603) at a room temperature for 20 min. Thereafter, nitrogen gas was blown on the both sides blowing off water to dryness. The silane coupling treatment was completed by baking the plate in an oven at 120° C. for 1 hour. Subsequently, 2.7 mg of EMCS (N-(6-maleimidoca-proyloxy) succinimide: Dojin Company) was weighed and dissolved in a 1:1 solution of DMSO/ethanol (final concentration: 0.3 mg/ml). The glass substrate treated with the silane coupling agent was soaked in this EMCS solution for 2 hours to react the amino group of the silane coupling agent with the succimide group of EMCS. At this stage, the maleimide group of EMCS is transferred to the glass surface. After that, the glass plate was washed with ethanol and dried with nitrogen gas to be used for a coupling reaction with the DNA.

3. Coupling of DNA to the Substrate

Synthesis of 64 DNA Probes

The above 64 types of probe DNAs each having an SH group (thiol group) at the 5' terminus were synthesized by Becks Co., Ltd. at our request.

Ejection of DNA Probes

The above 64 types of DNAs were ejected respectively as follows. Each DNA was dissolved in water and diluted with SG Clear (aqueous solution containing 7.5% of glycerin, 7.5% of urea, 7.5% of thiodiglycol and 1% of acetylenol EH) to a final concentration of 8 μM. Then 100 μl of this DNA solution was filled into a nozzle of a BJ printer Head BC 62 (Canon) modified to eject a small amount and to eject six solutions per head. Two heads were used at a time so that 12 types of DNAs could be ejected at once, and the heads were changed 6 times so that 64 spots of 64 types of DNAs were formed on the glass plates independently.

Sixty four probes were spotted with a diameter of 70 μm and a pitch of 200 μm to form a matrix of 8×8. After that, the plate was left standing in a humidified chamber for 30 min for a linking reaction of the probe DNA to the substrate.

Hybridization Reaction

Blocking Reaction

After completion of the reaction, the substrate was washed with a 1 M NaCl/50 mM phosphate buffer solution (pH 7.0) to wash out thoroughly the DNA solution on the glass surface. Then, this was soaked in an aqueous solution of 2% bovine serum albumin and allowed to stand for 2 hours to carry out a blocking reaction.

Preparation of Model Sample DNA

Rhodamine labeled DNA No. 1 (SEQ ID NO: 65) of the same length as the probes but having the normal sequence of p53 gene was prepared. The sequence is shown below and rhodamine is bonded to the 5' terminus.

No. 1: 5'Rho-ATGAACCGGAGGCCCATC3'

Hybridization Conditions

Two milliliters of a 10 nM model sample DNA solution containing 100 mM NaCl was applied to the DNA array substrate in a hybridization bag, and the bag was initially heated at 80° C. for 10 min. Then, the temperature of the incubator was lowered to 45° C. and the reaction was continued for 15 hours.

5. Detection

Detection Method

The detection was performed by connecting an image analysis processing apparatus, ARGUS (a product of Hamamatsu Photonics) to a fluorescence microscope (a product of Nicon).

Result

The fluorescence intensities obtained from the model hybridization reaction with the labeled DNA No. 1 (18-mer) are shown in FIG. 4. The maximum value of the fluorescence intensity was obtained at the spot of probe 42, which is fully complementary to DNA No. 1. Taking this intensity as the maximum value (1.0), the threshold is set at 10% of this value and the spots having higher intensity are painted dark.

The spots of probes 10, 26, 41, 46 and 58 of one-base mismatch hybrids have fluorescence higher than the threshold, and it is understood that the location coincides well with FIG. 2 of the expected pattern. By lowering the threshold further, in addition to the above 5 spots, the spots of other one-base mismatch probes appeared around the full matched probe in vertical and horizontal lines, coinciding with the expected pattern.

Example 2

Pattern Recognition II

A DNA array of 64 types of probes was prepared in the same manner as in Example 1, and the hybridization reaction was performed using a rhodamine-labeled DNA No. 2 as a model sample. The DNA No. 2 (SEQ ID NO: 66) has a sequence complementary to the No. 46 probe of FIG. 1.

No. 2: 5'Rho-ATGAACCAGAGGCCCATC3'

The reaction conditions of hybridization are the same as in Example 1.

Figure 5:
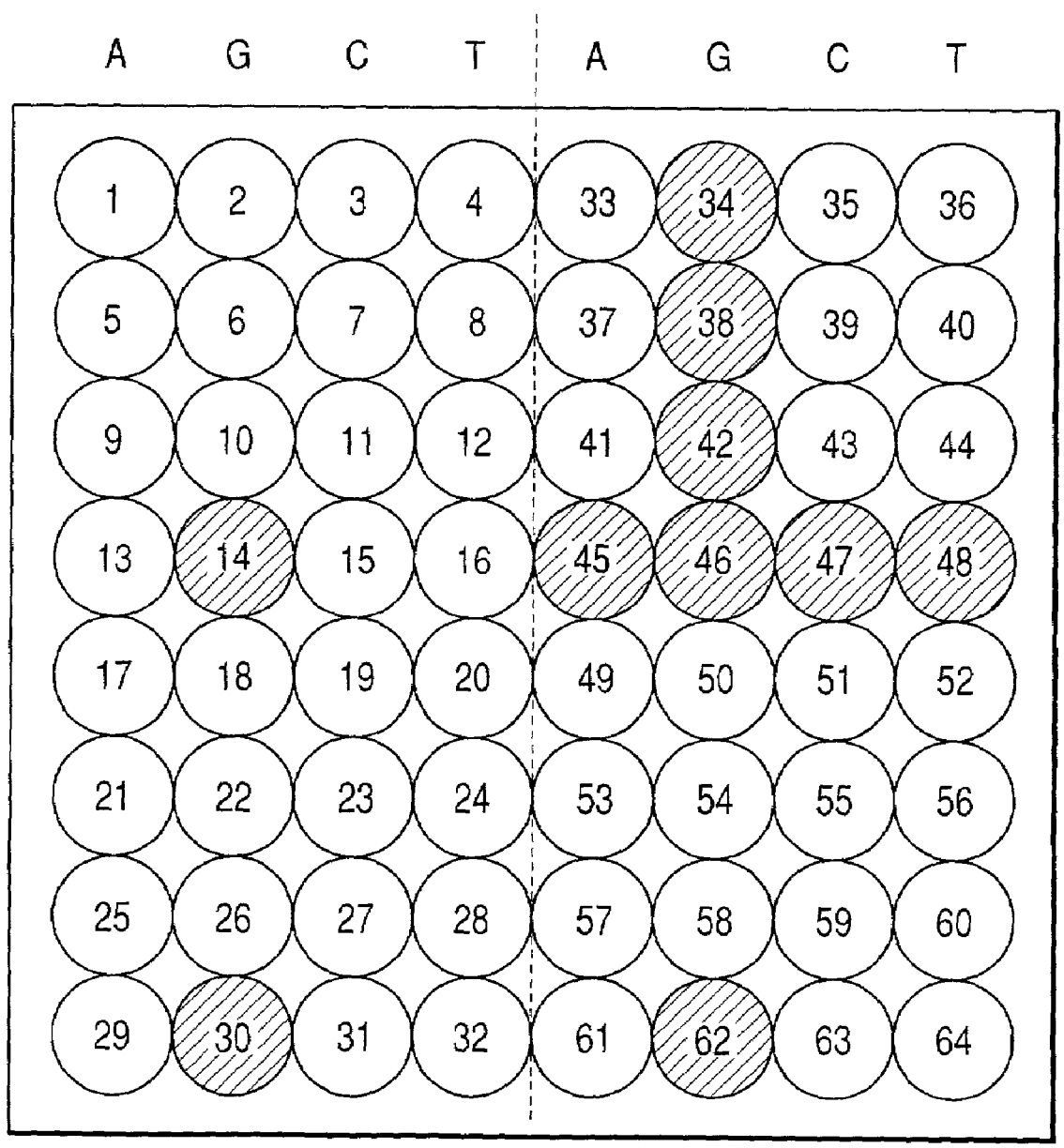
FIG. 5 is an expected pattern in Example 2.
Figure 6:
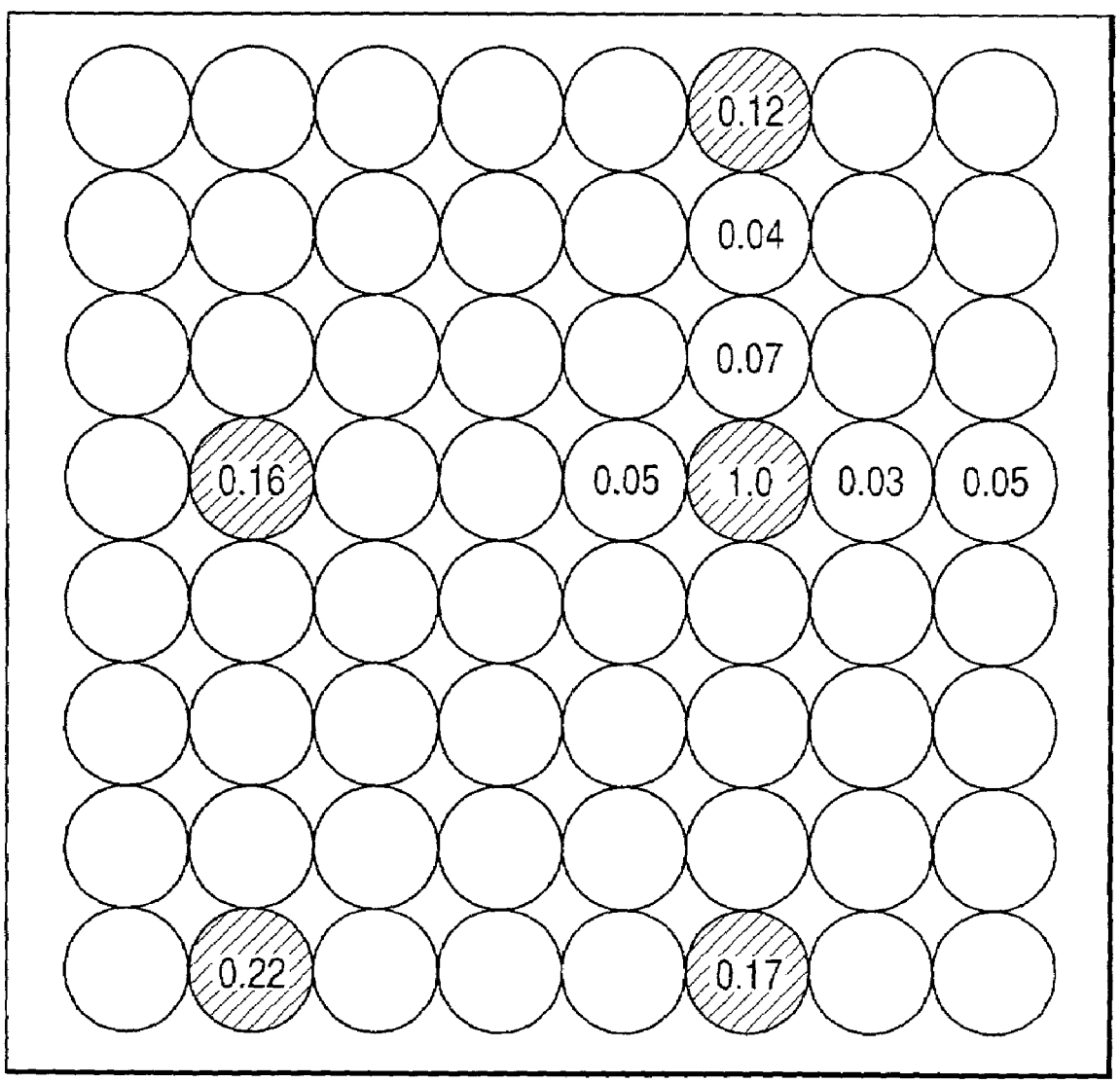
FIG. 6 is a pattern obtained in Example 2 with a fluorescence threshold of 10%.

FIG. 5 is an expected pattern consisting of the perfect match and one-base mismatch hybrids, and the resulted pattern obtained as in Example 1 is shown in FIG. 6. The threshold is set at 10% of the maximum value. When the detected spots are painted dark, the result corresponds well with the expectation.

Example 3

Pattern Recognition III

Figure 7:
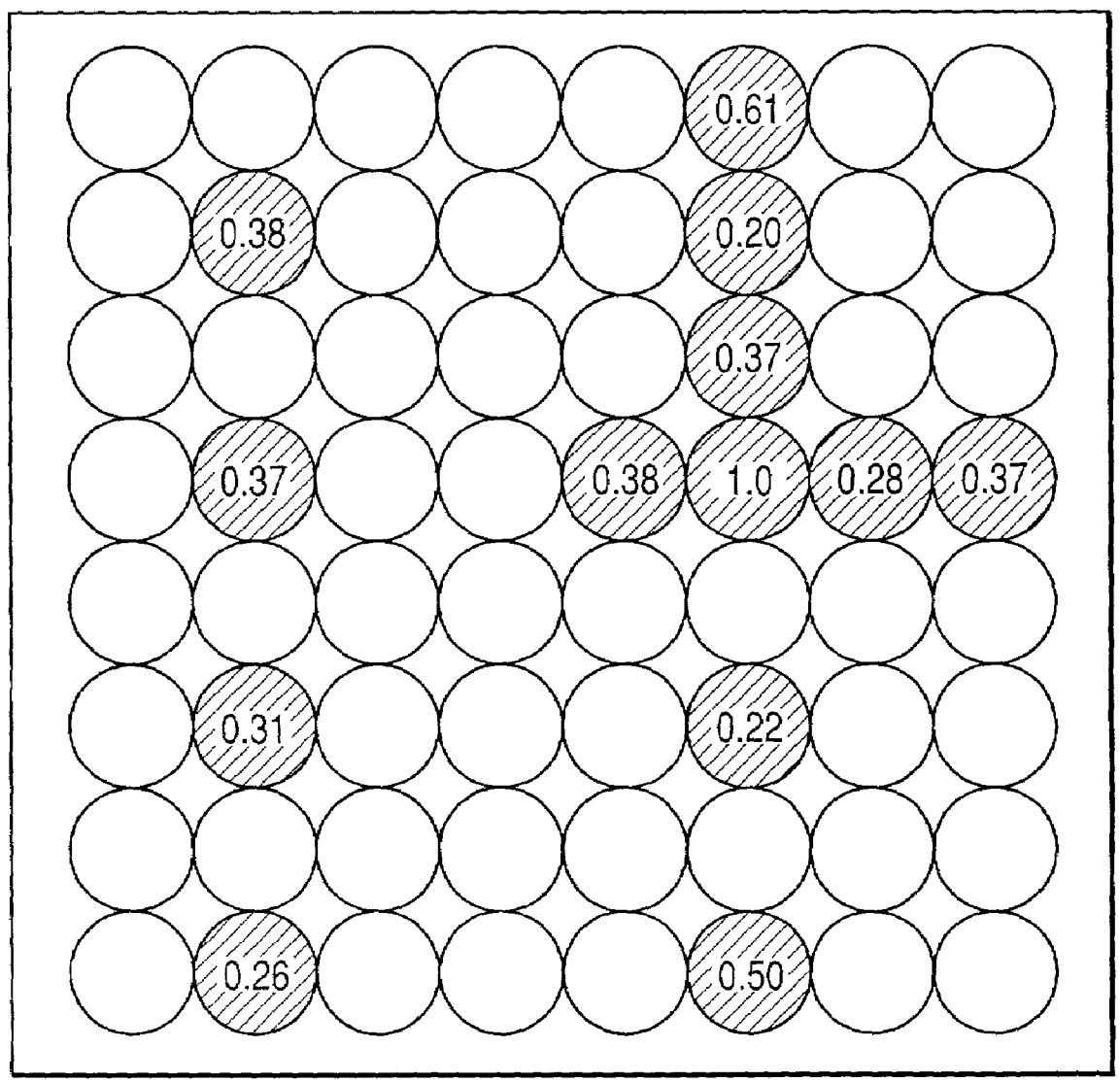
FIG. 7 is a pattern obtained in Example 3 with fluorescence intensities.

An experiment was carried out in the same manner as in Example 2, except that the concentration of the sample DNA used for the hybridization reaction was 5 nM and the reaction was carried out at 40° C. overnight. The result obtained is shown in FIG. 7.

If the threshold is set as 50%, fluorescence was detected at the positions (shaded parts) of Nos. 34 and 62 probes (one-base mismatch) in addition to No. 46 (full match), and with further reduction of the threshold to 10%, the result coincided with the expected pattern. In this case, Nos. 6, 22 and 54 of two-base mismatch probes were detected, but the two-base mismatch can be distinguished from the one-base mismatch as the deviation from the expected pattern of one-base mismatch, and No. 46 can be called as the full matched probe.

---

What is claimed is:

1. A method for identifying a base sequence present in a target single-stranded nucleic acid comprising the steps of:
   (a) preparing a probe array in which single-stranded nucleic acid probes of No. 1 to No. n (n≧3) are arranged as isolated spots on a substrate;
   (b) reacting a single-stranded nucleic acid which has a base sequence fully complementary to a base sequence of one of the single-stranded nucleic acid probes and is fluorescence-labeled, with the probe array under such conditions that single-stranded nucleic acids complementary to each other form a double-stranded nucleic acid;
   removing the unreacted labeled single-stranded nucleic acid; and
   measuring fluorescence intensity of each spot of the probe array to obtain a first template pattern showing a relationship between location of the probes and fluorescent characteristics;
   (c) analyzing the first template pattern to locate probes and to calculate a mean value of fluorescence intensities (Fi) of the double-stranded nucleic acids having i of mismatched base pairs, where i is an integer not less than 1;
   (d) determining a threshold value by calculating a difference (F1, 0) between the fluorescence intensity of the fully complementary double-stranded nucleic acid without mismatch (F0) and a mean value of fluorescence intensities of double-stranded nucleic acids having one-base mismatch (F1), and by further calculating a difference (Fi+1, i) between a mean value of fluorescence intensities of a double-stranded nucleic acid having (i+1) base mismatches (Fi+1) and the mean value of the fluorescence intensities of the double-stranded nucleic acids having i-base mismatches (Fi), and identifying i being Fi+1, i<<Fi, i−1, wherein the threshold value is set between the mean value of the fluorescence intensities having i-base mismatches (Fi) and the mean value of the fluorescence intensities having (i+1) mismatches (Fi+1);
   (e) preparing a second template pattern of positive probe spots of probes having base sequences differing from the base sequence of the second probe by i or less bases where i is determined in said step (d), wherein negative probe spots are probes having base sequences differing from the second probe by more than i bases;
   (f) performing the same operation as the step (e) for each of remaining single-stranded nucleic acid probes and obtaining template patterns of No. 3 to No. n showing a relationship between location and fluorescent characteristics of the probes;

(g) performing the same operation as the step (b) using a sample containing the target single-stranded nucleic acid of the base sequence to obtain a sample pattern showing a relationship between a position and fluorescent characteristics, wherein the sample pattern is obtained by using the threshold value;

(h) comparing the sample pattern obtained in the step (g) with a plurality of template patterns, the plurality of template patterns comprising the first and second template patterns and the template patterns of No. 3 to No. n, to find a template pattern substantially identical to the sample pattern; and (i) determining the base sequence of the target single-stranded nucleic acid to be a base sequence complementary to the base sequence of the probe taken for the preparation of the template pattern found in the step (h).

2. The method according to claim 1, wherein the length of each of the single-stranded nucleic acid probes is 8 mer to 30 mer.

3. The method according to claim 2, wherein the length of each of the single-stranded nucleic acid probes is 12 mer to 25 mer.

4. The method according to claim 1, wherein the number of the mismatched base pairs (i) is 1.

5. A method for identifying a base sequence present in a target nucleic acid by using a DNA chip in which a plurality of probes are arranged, comprising the steps of:

reacting a target nucleic acid which has a known base sequence and is fluorescence-labeled, with the DNA chip and then observing the DNA chip after the reaction to obtain a template pattern showing a relationship between the probe location and the fluorescence intensity;

reacting a target nucleic acid which has an unknown base sequence and is fluorescence-labeled, with the DNA chip and then observing the DNA chip after the reaction to obtain a sample pattern showing a relationship between the probe location and the fluorescence intensity; and comparing the sample pattern with the template pattern to thereby determine whether the unknown base sequence agrees with the known base sequence, wherein a threshold value is determined by calculating a difference between a mean value of fluorescence intensities of i-base mismatches and a mean value of fluorescence intensities of i+1 mismatches, where i is an integer not less than 1, and is set between the mean value of fluorescence intensities of i-base mismatches and the mean value of fluorescence intensities of i+1 mismatches, such that a probe location showing a fluorescence intensity above the threshold value is defined to be positive while a probe location otherwise is defined to be negative, and the template pattern and the sample pattern are prepared by adopting only positive probe locations.

6. The method according to claim 5, wherein i is 1.

* * * * *

UNITED STATES PATENT AND TRADEMARK OFFICE
CERTIFICATE OF CORRECTION

| | | |
|---|---|---|
| PATENT NO. | : 7,273,697 B2 | |
| APPLICATION NO. | : 09/942596 | |
| DATED | : September 25, 2007 | |
| INVENTOR(S) | : Yamamoto et al. | |

It is certified that error appears in the above-identified patent and that said Letters Patent is hereby corrected as shown below:

Title Page;

COVER SHEET:
After William I. Wood, et al., "Tetramethylamonium" should read
-- Tetramethylammonium --.

COLUMN 1:
Line 36, "prove" should read -- probe --;
Line 60, "full" should read -- fully --; and
Line 62, "full" should read --fully--.

COLUMN 2:
Line 45, "an" should read -- a --.

COLUMN 5:
Line 9, "invention" should read -- invention is --.

COLUMN 6:
Line 31, "not" should read -- do not --.

COLUMN 8:
Table 1, SEQ ID NO: 15, "GATGGGACTCTGGTTCAT" should read
-- GATGGGACTCTCGTTCAT--.

COLUMN 9:
Table 1, SEQ ID NO: 25, "GATGGGGCTGCAGTTCAT" should read
-- GATGGGGCTCCAGTTCAT --; and
Table 1, SEQ ID NO. 47, "GATGGGCCTGTCGTTCAT" should read
-- GATGGGCCTCTCGTTCAT --.

UNITED STATES PATENT AND TRADEMARK OFFICE
CERTIFICATE OF CORRECTION

PATENT NO. : 7,273,697 B2
APPLICATION NO. : 09/942596
DATED : September 25, 2007
INVENTOR(S) : Yamamoto et al.

It is certified that error appears in the above-identified patent and that said Letters Patent is hereby corrected as shown below:

COLUMN 10:
Line 34, "Sixty four" should read -- Sixty-four --; and
Line 67, "Nicon)." should read -- Nikon). --.

Signed and Sealed this

Thirteenth Day of May, 2008

JON W. DUDAS
*Director of the United States Patent and Trademark Office*

SEQUENCE LISTING

```
<160> NUMBER OF SEQ ID NOS: 66

<210> SEQ ID NO 1
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 1
gatgggactc aagttcat                                                18

<210> SEQ ID NO 2
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 2
gatgggactc aggttcat                                                18

<210> SEQ ID NO 3
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 3
gatgggactc acgttcat                                                18
```

-continued

<210> SEQ ID NO 4
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 4
gatgggactc atgttcat                                                   18

<210> SEQ ID NO 5
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 5
gatgggactc gagttcat                                                   18

<210> SEQ ID NO 6
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 6
gatgggactc gggttcat                                                   18

<210> SEQ ID NO 7
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 7
gatgggactc gcgttcat                                                   18

<210> SEQ ID NO 8
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 8
gatgggactc gtgttcat                                                   18

<210> SEQ ID NO 9
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 9
gatgggactc cagttcat                                                   18

<210> SEQ ID NO 10
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 10
gatgggactc cggttcat                                                          18

<210> SEQ ID NO 11
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 11
gatgggactc ccgttcat                                                          18

<210> SEQ ID NO 12
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 12
gatgggactc ctgttcat                                                          18

<210> SEQ ID NO 13
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 13
gatgggactc tagttcat                                                          18

<210> SEQ ID NO 14
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 14
gatgggactc tggttcat                                                          18

<210> SEQ ID NO 15
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 15
gatgggactc tcgttcat                                                          18

<210> SEQ ID NO 16
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 16
gatgggactc ttgttcat                                                          18

<210> SEQ ID NO 17

<211> LENGTH: 18
<212> TYPE: DNA
<213> ORGANISM: Artificial sequence
<220> FEATURE:
<223> OTHER INFORMATION: Sample oligonucleotide

<400> SEQUENCE: 17
gatggggctc aagttcat                                                18

<210> SEQ ID NO 18
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 18
gatggggctc aggttcat                                                18

<210> SEQ ID NO 19
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 19
gatggggctc acgttcat                                                18

<210> SEQ ID NO 20
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 20
gatggggctc atgttcat                                                18

<210> SEQ ID NO 21
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 21
gatggggctc gagttcat                                                18

<210> SEQ ID NO 22
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 22
gatggggctc gggttcat                                                18

<210> SEQ ID NO 23
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 23

```
gatggggctc gcgttcat                                              18

<210> SEQ ID NO 24
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 24
gatggggctc gtgttcat                                              18

<210> SEQ ID NO 25
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 25
gatggggctc cagttcat                                              18

<210> SEQ ID NO 26
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 26
gatggggctc cggttcat                                              18

<210> SEQ ID NO 27
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 27
gatggggctc ccgttcat                                              18

<210> SEQ ID NO 28
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 28
gatggggctc ctgttcat                                              18

<210> SEQ ID NO 29
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 29
gatggggctc tagttcat                                              18

<210> SEQ ID NO 30
<211> LENGTH: 18
<212> TYPE: DNA
```

```
<213> ORGANISM: Artificial sequence
<220> FEATURE:
<223> OTHER INFORMATION: Sample oligonucleotide

<400> SEQUENCE: 30
gatggggctc tggttcat                                                    18

<210> SEQ ID NO 31
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 31
gatggggctc tcgttcat                                                    18

<210> SEQ ID NO 32
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 32
gatggggctc ttgttcat                                                    18

<210> SEQ ID NO 33
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 33
gatgggcctc aagttcat                                                    18

<210> SEQ ID NO 34
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 34
gatgggcctc aggttcat                                                    18

<210> SEQ ID NO 35
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 35
gatgggcctc acgttcat                                                    18

<210> SEQ ID NO 36
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 36
gatgggcctc atgttcat                                                    18
```

-continued

<210> SEQ ID NO 37
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 37
gatgggcctc gagttcat                                                 18

<210> SEQ ID NO 38
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 38
gatgggcctc gggttcat                                                 18

<210> SEQ ID NO 39
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 39
gatgggcctc gcgttcat                                                 18

<210> SEQ ID NO 40
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 40
gatgggcctc gtgttcat                                                 18

<210> SEQ ID NO 41
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 41
gatgggcctc cagttcat                                                 18

<210> SEQ ID NO 42
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 42
gatgggcctc cggttcat                                                 18

<210> SEQ ID NO 43
<211> LENGTH: 18
<212> TYPE: DNA
<213> ORGANISM: Artificial sequence
<220> FEATURE:

```
<223> OTHER INFORMATION: Sample oligonucleotide

<400> SEQUENCE: 43
gatgggcctc ccgttcat                                                 18

<210> SEQ ID NO 44
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 44
gatgggcctc ctgttcat                                                 18

<210> SEQ ID NO 45
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 45
gatgggcctc tagttcat                                                 18

<210> SEQ ID NO 46
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 46
gatgggcctc tggttcat                                                 18

<210> SEQ ID NO 47
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 47
gatgggcctc tcgttcat                                                 18

<210> SEQ ID NO 48
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 48
gatgggcctc ttgttcat                                                 18

<210> SEQ ID NO 49
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 49
gatgggtctc aagttcat                                                 18
```

```
<210> SEQ ID NO 50
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 50
gatgggtctc aggttcat                                                 18

<210> SEQ ID NO 51
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 51
gatgggtctc acgttcat                                                 18

<210> SEQ ID NO 52
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 52
gatgggtctc atgttcat                                                 18

<210> SEQ ID NO 53
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 53
gatgggtctc gagttcat                                                 18

<210> SEQ ID NO 54
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 54
gatgggtctc gggttcat                                                 18

<210> SEQ ID NO 55
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 55
gatgggtctc gcgttcat                                                 18

<210> SEQ ID NO 56
<211> LENGTH: 18
<212> TYPE: DNA
<213> ORGANISM: Artificial sequence
<220> FEATURE:
<223> OTHER INFORMATION: Sample oligonucleotide
```

-continued

<400> SEQUENCE: 56
gatgggtctc gtgttcat                                                 18

<210> SEQ ID NO 57
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 57
gatgggtctc cagttcat                                                 18

<210> SEQ ID NO 58
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 58
gatgggtctc cggttcat                                                 18

<210> SEQ ID NO 59
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 59
gatgggtctc ccgttcat                                                 18

<210> SEQ ID NO 60
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 60
gatgggtctc ctgttcat                                                 18

<210> SEQ ID NO 61
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 61
gatgggtctc tagttcat                                                 18

<210> SEQ ID NO 62
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 62
gatgggtctc tggttcat                                                 18

<210> SEQ ID NO 63
<211> LENGTH: 18

```
<212> TYPE: DNA
<213> ORGANISM: Artificial sequence
<220> FEATURE:
<223> OTHER INFORMATION: Sample oligonucleotide

<400> SEQUENCE: 63
gatgggtctc tcgttcat                                                 18

<210> SEQ ID NO 64
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 64
gatgggtctc ttgttcat                                                 18

<210> SEQ ID NO 65
<211> LENGTH: 18
<212> TYPE: DNA
<213> ORGANISM: p53 fragment
<220> FEATURE:
<223> OTHER INFORMATION: Sample oligonucleotide

<400> SEQUENCE: 65
atgaaccgga ggcccatc                                                 18

<210> SEQ ID NO 66
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 66
atgaaccaga ggcccatc                                                 18
```